US00PP26026P3

(12) United States Plant Patent
Bornstein

(10) Patent No.: US PP26,026 P3
(45) Date of Patent: Oct. 27, 2015

(54) ***GYPSOPHILA* PLANT NAMED 'PEARLS PETITE'**

(50) Latin Name: ***Gypsophila paniculata* L.**
Varietal Denomination: Pearls Petite

(71) Applicant: M.D. Gypsophila Breeding Ltd, Negev (IL)

(72) Inventor: Menachem Bornstein, Holon (IL)

(73) Assignee: SELECTA CUT FLOWERS S.A.U., Barcelona (ES)

( * ) Notice: Subject to any disclaimer, the term of this patent is extended or adjusted under 35 U.S.C. 154(b) by 92 days.

(21) Appl. No.: 13/999,340

(22) Filed: Feb. 12, 2014

(65) Prior Publication Data
US 2015/0230383 P1 Aug. 13, 2015

(51) Int. Cl.
*A01H 5/02* (2006.01)

(52) U.S. Cl.
USPC ..... Plt./354

(58) Field of Classification Search
USPC ..... Plt./354
See application file for complete search history.

*Primary Examiner* — Susan McCormick Ewoldt
(74) *Attorney, Agent, or Firm* — Barbara Campbell; James M. Weatherly; Cochran Freund & Young LLC

(57) ABSTRACT

A new *Gypsophila* plant particularly distinguished by having small, semi-double, white flowers and an upright shrub form type, is disclosed.

2 Drawing Sheets

Genus and species: *Gypsophila paniculata* L.
Variety denomination: 'Pearls Petite'.

BACKGROUND OF THE NEW PLANT

The present invention comprises a new and distinct variety of *Gypsophila*, botanically known as *Gypsophila paniculata* L., and hereinafter referred to by the variety name 'Pearls Petite'. 'Pearls Petite' originated from an open pollination within a group of unmarked parental lines in April 2010 in Negev, Israel.

Seeds were obtained from the open pollination and sown. Plants were then grown for evaluation. A plant line was selected in August 2010 in Negev, Israel and named 'Pearls Petite'. In September 2010, 'Pearls Petite' was first vegetatively propagated in Negev, Israel by side shoot cuttings. 'Pearls Petite' was found to reproduce true to type in successive generations of asexual propagation via side shoot cuttings in Negrev, Israel.

SUMMARY

The following are the most outstanding and distinguishing characteristics of this new variety when grown under normal horticultural practices in Negev, Israel.

1. Small, semi-double, white flowers; and
2. An upright shrub form type.

DESCRIPTION OF THE PHOTOGRAPHS

This new *Gypsophila* plant is illustrated by the accompanying photographs. The photographs were taken in Negev, Israel as described below. The colors shown are as true as can be reasonably obtained by conventional photographic procedures.

DESCRIPTION OF THE NEW VARIETY

Figure 1:
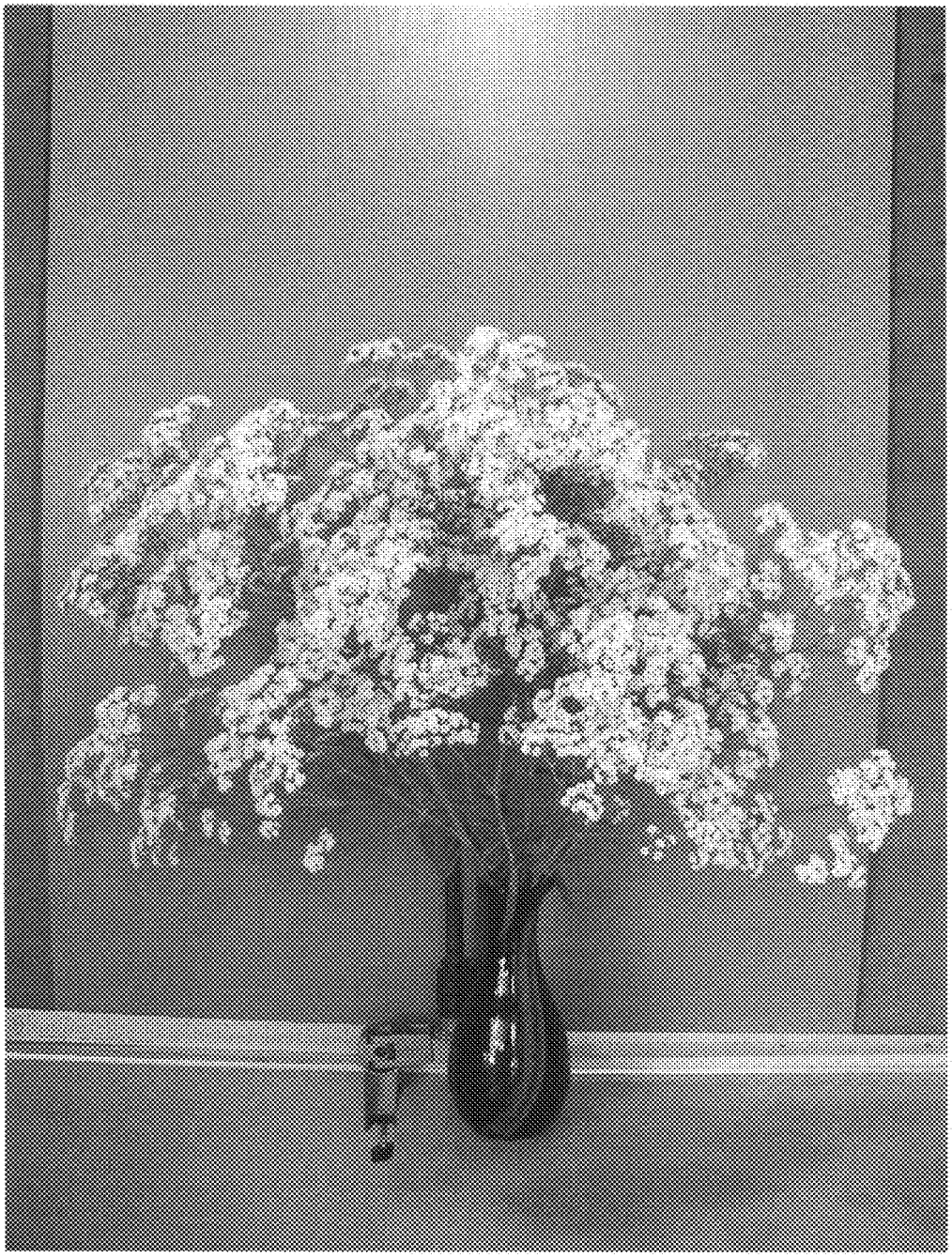
FIG. 1 shows ten cut flowering stems of the plant in a vase from the summer of 2011.
Figure 2:
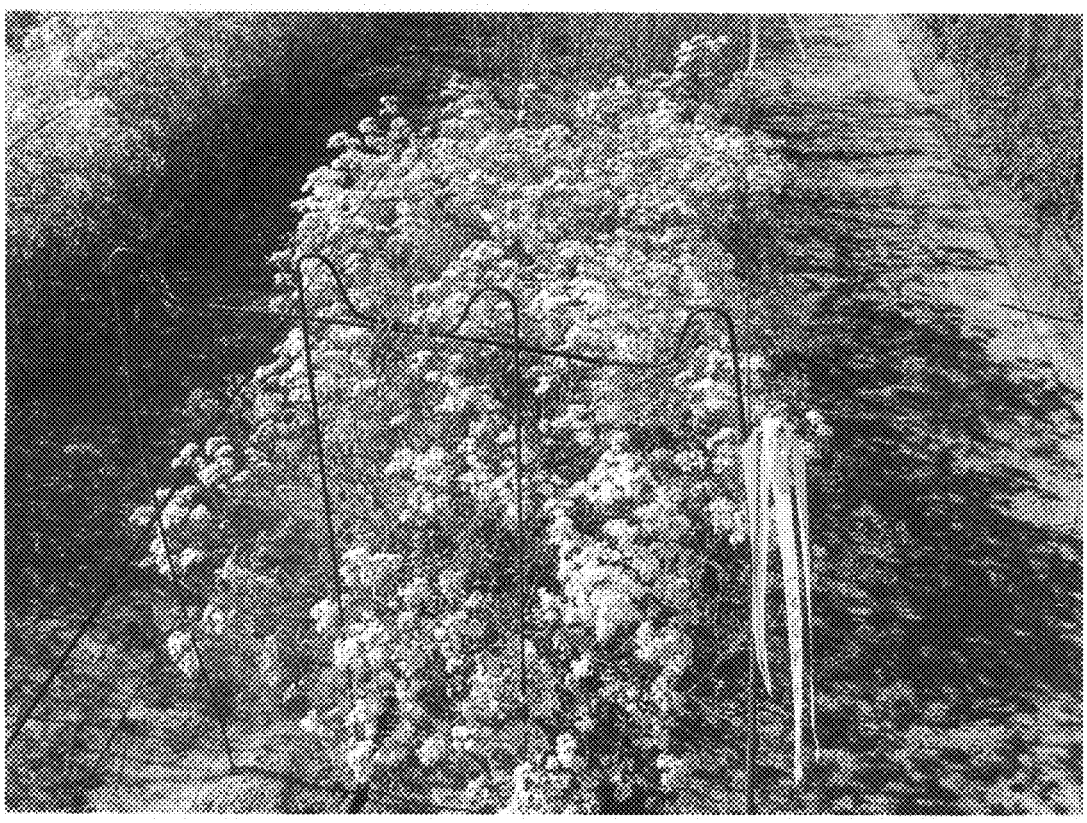
FIG. 2 shows a plant ten-weeks from planting grown in an open field in Negev, Israel in the autumn of 2012.

The following detailed descriptions set forth the distinctive characteristics of 'Pearls Petite'. The data which define these characteristics were collected in Negev, Israel in the summer of 2013. Data was collected on plants ten-weeks after planting. Color references are to The R.H.S. Colour Chart of The Royal Horticultural Society of London (R.H.S.) (1986).

Classification:
- *Family*.—Caryophyllaceae.
- *Botanical*.—*Gypsophila paniculata* L.
- *Common name*.—Baby's Breath.
- *Denomination*.—'Pearls Petite'.

Parentage:
- *Female parent*.—Unnamed *Gypsophila paniculata* L. plant.
- *Male parent*.—Unnamed *Gypsophila paniculata* L. plant.

Plant:
- *Form*.—Upright shrub type.
- *Habit*.—Perennial.
- *Plant height*.—55.0 cm to 65.0 cm.
- *Plant width*.—50.0 cm to 55.0 cm.
- *Flowering habit*.—Year round in periodic flushes depending on growing conditions.
- *Time to produce a finished flowering plant*.—4 weeks rooting, 1 week hardening, 8 to 12 weeks between planting and first flowering depending on weather.
- *Propagation type*.—Vegetative by side shoots cuttings.
- *Time to initiate roots*.—2 to 3 weeks. Plant ready for planting in 5 weeks under moderate climate.
- *Root description*.—Light brown, branched, fibrillary secondary roots.

Flowering stems:
*Quantity per plant.*—10 to 15 per flush commercial grade.
*Color.*—RHS 146B (Yellow-Green).
*General description.*—Compound cymes with numerous flowers, panicle shaped.
*Stem strength.*—Stable.
*Length.*—55.0 cm to 65.0 cm.
*Diameter.*—50.0 cm to 55.0 cm.
*Internodes length.*—3.0 cm to 4.0 cm at stem base.
*Texture.*—Glabrous.

Leaves:
*Arrangement.*—Opposite.
*Shape.*—Lanceolate.
*Apex.*—Acute.
*Base.*—Wedge shaped.
*Margin.*—Entire.
*Color.*—Both mature and immature leaves: Upper surface: RHS 147A (Yellow-Green). Lower surface: RHS 147B (Yellow-Green).
*Length.*—6.5 cm to 7.0 cm.
*Width.*—0.6 cm to 0.7 cm.
*Texture.*—Rugulose.
*Venation pattern.*—Parallel.
*Venation color.*—Upper surface: RHS 147A (Yellow-Green). Lower surface: RHS 147B (Yellow-Green).

Flowers:
*Inflorescence type.*—Compound cymes with numerous flowers having a panicle shape.
*Flowering season.*—Year round naturally under 12 hours (and above) light.
*Lastingness of individual flowers on the plant.*—7 to 10 days.
*Lastingness of the flowers as a cut flower.*—7 to 10 days when proper post-harvest treatments are applied.
*Flower width.*—0.6 cm to 0.7 cm.
*Flower depth.*—0.5 cm.
*Flower shape.*—Oblate, consists of many petals (semi-double type).
*Fragrance.*—Typical for *Gypsophila.*
*Number of inflorescences per plant.*—10 to 15 per flush commercial grade.
*Number of flowers per inflorescence.*—Hundreds; varies according to what you define a commercial stem and the way of cultivation.

Inflorescence:
*Length (height).*—55.0 cm to 65.0 cm.
*Diameter.*—50.0 cm to 55.0 cm.

Pedicel:
*Length.*—0.5 cm.
*Diameter.*—0.05 cm.
*Strength.*—Stable.
*Texture.*—Fine pubescent.
*Color.*—RHS 147C (Yellow-Green).

Peduncle:
*Length.*—55.0 cm to 65.0 cm.
*Diameter.*—0.2 cm to 0.3 cm at plant base.
*Texture.*—Glabrous.
*Color.*—RHS 146B (Yellow-Green).

Flower buds: Fully mature.
*Color.*—RHS 155C (White).
*Shape.*—Oblate.
*Length.*—0.3 cm.
*Diameter.*—0.2 cm.

Petals:
*Arrangement.*—Pompon.
*Quantity.*—30 to 40 per flower.
*Shape.*—Spathulate.
*Apex.*—Emarginated to wavy.
*Base.*—Cuneate.
*Margin.*—Entire.
*Size.*—Length: 0.2 cm. Width: 0.1 cm.
*Color.*—When opening: Both upper and lower surfaces: RHS 155C (White). Fully opened: Both upper and lower surfaces: RHS 155C (White).
*Surface texture.*—Both upper and lower surfaces: Smooth.

Sepals:
*Arrangement.*—Cup shaped.
*Quantity.*—5.
*Shape.*—Lanceolate.
*Apex.*—Acute.
*Base.*—Cuneate.
*Margin.*—Entire.
*Length.*—0.2 cm.
*Width.*—0.1 cm.
*Color.*—Upper surface: Hidden; too difficult to determine color. Lower surface: RHS 147C (Yellow-Green).
*Surface texture.*—Upper surface: Hidden; too difficult to determine texture. Lower surface: Glabrous.

Reproductive organs:
*Stamens.*—Quantity per flower: 5 to 10. Anther shape: Ovoid. Anther length: 0.1 cm to 0.2 cm. Anther color: RHS 156A (Greyed-White). Pollen amount: Cannot be defined, at best, scarce. Pollen color: RHS 156A (Greyed-White).
*Pistils.*—Quantity per flower: 2. Pistil length: 0.4 cm to 0.5 cm. Style length: 0.4 cm to 0.5 cm. Style color: RHS 155C (White). Stigma shape: Ovoid. Stigma color: RHS 156C (Greyed-White). Ovary color: Variegated green and purple; colors cannot be determined.

Fruit and seed set: None observed.

Disease and insect resistance: Good tolerance to die-back, powdery mildew and leaf miners.

COMPARISON WITH KNOWN VARIETY

'Pearls Petite' is a distinct variety of *Gypsophila* and is most similar to the *Gypsophila* commercial line 'Million Stars' (patent status unknown). Differences between the two varieties are described in Table 1:

TABLE 1

Comparison with Similar Variety

| Trait | Variety 'Pearls Petite' | Commercial line 'Million Stars' |
|---|---|---|
| Flower size | 0.6 cm to 0.7 cm | 0.5 cm to 0.6 cm |
| Flower type during summer time in Israel | Semi-double | Double |

I claim:

1. A new and distinct variety of *Gypsophila* plant named 'Pearls Petite' as shown and described herein.

* * * * *